(12) United States Patent
Williams

(10) Patent No.: US 6,231,856 B1
(45) Date of Patent: May 15, 2001

(54) METHODS AND COMPOSITIONS FOR TREATMENT OF AUTOIMMUNE DISEASES

(75) Inventor: Ralph Williams, Gainesville, FL (US)

(73) Assignee: University of Florida, Gainesville, FL (US)

(*) Notice: Subject to any disclaimer, the term of this patent is extended or adjusted under 35 U.S.C. 154(b) by 0 days.

(21) Appl. No.: 09/164,241

(22) Filed: Sep. 30, 1998

Related U.S. Application Data (63) Continuation of application No. 08/764,679, filed on Dec. 11, 1996, now abandoned.

(51) Int. Cl.$^7$ .................................................. A61K 39/395

(52) U.S. Cl. ...................................... 424/131.1; 424/133.1; 530/387.2; 530/387.3; 530/866; 530/868

(58) Field of Search ............................... 424/131.1, 133.1; 530/387.2, 387.3, 868, 866

(56) References Cited

U.S. PATENT DOCUMENTS

| | | |
|---|---|---|
| 4,690,905 | 9/1987 | Diamond et al. . |
| 4,925,787 * | 5/1990 | Tanihara et al. ...................... 435/7.1 |
| 5,096,704 | 3/1992 | Coffman et al. . |

OTHER PUBLICATIONS

The Merck Manual of Diagnosis and Therapy 16$^{th}$ Edition pp. 339–340, 1211–1212, 1992.*
Aster et al. Amer. J. of Hematology, vol. 58 231–234, 1998.*
Berchtold et al., Blood, vol. 74 No. 7: 2414–2417, 1989.*
The Merck Manual, 16$^{th}$ Ed., Merck Research Laboratories Merck & Co. Rahway N.J., 1992 pp. 1211–1212.*
Akashi, K. et al. (1990) Successful treatment of refractory systemic lupus erythematosus with intravenous immuno--globulins. J. Rheumatology 17: 375–379.

Blalock, J.E. (1990) Complementarity of peptides specified by "sense" and "antisense" strands of DNA. Trends in Biotechnol. 8: 140–144.
Davidson, A. et al. (1990) Molecular characterization of a somatically–mutated anti–DNA antibody bearing two systemic lupus erythematosus–related idiotypes. J. Clin. Invest. 85: 1401–1409.
Ebling, F., B.H. Hahn (1980) Restricted subpopulations of anti–DNA antibodies in kidney of mice with systemic lupus: comparison of antibodies in serum and renal eluates. Arthritis Rheum. 23: 392–403.
Gallo, G.R. et al. (1981) Charge of circulating immune complexes as a factor in glomerular basement membrane localization. J. Clin. Invest. 67: 1305–1313.
Gauthier, V.J. et al. (1982) Effect of cationized antibodies in preformed immune complexes on deposition and persistence in renal glomeruli. J. Exp. Med. 156: 766–777.
Jordan, S.C. (1989) Intravenous gamma globulin therapy in systemic lupus erythematosus and immune complex disease. Clin. Immunol. Immunopathol. 53: S164–169.

(List continued on next page.)

Primary Examiner—Patrick Nolan
(74) Attorney, Agent, or Firm—Gerald H. Bencen; Timothy H. Van Dyke; Bencen & Van Dyke, P.A.

(57) ABSTRACT

The subject invention concerns a method for therapeutically treating a patient afflicted with autoimmune disorders or disease. The subject method comprises admninistering to a patient an antibody composition that is capable of binding to and inhibiting self-reactive pathogenic anti-bodies present within the patient. Specifically exemplified is a method for treating systemic lupus erythematosus wherein the antibody composition administered to the patient comprises purified anti-DNA anti-idiotypic antibodies. The subject invention further concerns a method for purifying from pooled human gamma globulin preparations anti-idiotype antibodies useful in the present therapeutic method. The present invention further concerns a purified antibody composition useful in the present therapeutic method.

2 Claims, 6 Drawing Sheets

OTHER PUBLICATIONS

Maier, C.C. et al. (1994) Identification of interactive determinants on idiotypic–anti–idiotypic antibodies through comparison of their hydropathic profiles. Complementary peptides: application in immunology and as antibody mimetics. ImmunoMethods 5: 107–113.

Mouthon, L. et al. (1996) Mechanisms of action of intravenous immune globulin in immune–mediated diseases. Clin. Exp. Immunol. 104(suppl.1):3–9.

Shoenfeld, Y. et al. (1989) Short analytical review: the role of the human anti–DNA idiotype 16/6 in autoimmunity. Clin. Immunol. Immunopathol. 51: 313–315.

Silvestris, F. et al. (1996) Intravenous immune globulin therapy of lupus nephritis: use of pathogenic anti–DNA–reactive IgG. Clin. Exp. Immunol. 104(Suppl. 1):91–97.

Silvestris, F. et al. (1984) Studies of anti–F(ab')$_2$ antibodies and possible immunologic control mechanisms in systemic lupus. Arthritis Rheum. 27: 1387–1396.

Silvestris, F., P. Cafforio, F. Dammacco (1994) Pathogenic anti–DNA idiotype–reactive IgG in intravenous immunoglobulin preparations. Clin. Exp. Immunol. 97: 10–25.

Williams, Jr., R.C. et al. (1995a) Active SLE is associated with depletion of the natural generic anti–Id (anti–F(ab')$_2$) system. J. Rheumatol. 22: 1075–1088.

Williams, Jr., R.C. et al. (1995b) CDR molecular localization of possible anti–DNA antibodies in normal subjects, SLE patients and SLE first–degree relatives. J. Lab. and Clin. Med. 126: 44–56.

Williams, Jr., R.C. et al. (1994) Expression of F4, 8.12, 31 and 16/6 anti–DNA idiotype–related antigens on cationic human IgG myeloma proteins. Clinical Immunology & Immunopathol. 73: 215–223.

Williams, Jr., R.C. et al. (1995c) Human IgG anti–F(ab')2 antibody cross reacts with DNA and other nuclear antigens. Arthritis Rheum. 38: 730, S275.

Blank, M. et al. (1994) Suppression of experimental systemic lupus erythematosus (SLE) with specific anti–idiotypic antibody–saporin conjugate. Clin. Exp. Immunol. 98: 434–441.

* cited by examiner

METHODS AND COMPOSITIONS FOR TREATMENT OF AUTOIMMUNE DISEASES

This applicaiton is a continuation of application Ser. No. 08/764,679, filed on Dec. 11, 1996, now abandoned.

This invention was made with government support under National Institutes of Health grant number AR 1382-42A1. The government has certain rights in the invention.

BACKGROUND OF THE INVENTION

Autoimmune diseases, such as systemic lupus erythematosus (SLE), myasthenia gravis (MG) and idiopathic thrombocytopenic purpura (ITP), among others, remain clinically important diseases in humans. As the name implies, autoinmune diseases wreak their havoc through the body's own immune system. While the pathological mechanisms differ between individual types of autoimmune diseases, one general mechanism involves the binding of certain antibodies (referred to herein as self-reactive antibodies or autoantibodies) present in the sera of patients to self nuclear or cellular antigens.

SLE has an incidence of about 1 in 700 women between the ages of 20 and 60. SLE can affect any organ system and can cause severe tissue damage. Numerous autoantibodies of differing specificity are present in SLE. SLE patients often produce autoantibodies having anti-DNA, anti-Ro, and anti-platelet specificity and which are capable of initiating clinical features of the disease, such as glomerulonephritis, arthritis, serositis, complete heart block in newborns, and hematologic abnormalities. These autoantibodies are also possibly related to central nervous system disturbances. Kidney damage, measured by the amount of proteinuria in the urine, is one of the most acute areas of damage associated with pathogenicity in SLE, and accounts for at least 50% of the mortality and morbidity of the disease. The presence of antibodies immunoreactive with double-stranded native DNA is used as a diagnostic marker for SLE.

Antibodies are composed of heavy and light polypeptide chains which are joined by disulfide bridges. Antibodies are divided into different classes according to their heavy chain structure; antibodies belonging to the same class are referred to as isotypes of each other. In addition, antibodies of a given isotype can be divided into subtypes. Antigenic determinants on antibodies that differ among animals that have inherited different alleles are referred to as allotopes; antibodies that share an allotope are referred to as members of the same allotype. Another type of antigenic determinant present on antibody molecules are those found primarily in the hypervariable region of the antigen binding site of the antibody. These determinants are referred to as idiotopes; antibodies that share an idiotope are referred to as members of the same idiotype. Idiotypic determinants are controlled by both genetic and antigenic influences. Antibodies having common or shared idiotypes generally exhibit the same antigenic specificity. However, antibodies from genetically dierent individuals which share a common antigenic specificity may exhibit idiotypic heterogeneity but, in some instances, show a major cross-reactive antigenic determinant. Thus, antibodies which bind the same antigen may have distinct idiotypic determinants, but also may share cross-reacting properties.

Currently, there are no really curative treatments for patients that have been diagosed with SLE. From a practical standpoint, physicians generally employ a number of powerful immunosuppressive drugs such as high-dose corticosteroids, azathioprine or cyclophosphamide—many of which have potentially harmful side effects to the patients being treated. In addition, these immunosuppressive drugs interfere with the person's ability to produce all antibodies, not just the self-reactive anti-DNA antibodies. Immunosuppressants also weaken the body's defense against other potential pathogens thereby making the patient extremely susceptible to infection and other potentially fatal diseases, such as cancer. In some of these instances, the side effects of current treatment modalities can be fatal.

One method of treatment for SLE, described in Diamond et al (U.S. Pat. No. 4,690,905), consists of generating monoclonal antibodies against anti-DNA antibodies (the monoclonal antibodies being referred to therein as anti-idiotypic antibodies) and then using these anti-idiotypic antibodies to remove the pathogenic anti-DNA antibodies from the patient's system. However, there are several drawbacks to this approach. For example, the removal of large quantities of blood for treatment can be a dangerous, complicated process. Essentially, blood is removed from a patient, treated to remove the anti-DNA antibodies, and then the treated blood returned to the patient. Such a removal technique would be similar to that used for hemodialysis, i.e., via an arterial passage. This type of treatment would be inconvenient (a qualified professional would be required to conduct treatment regularly), expensive, painful, and in some instances might subject the patient to a risk of infection and/or hemorrhaging, as well as depletion of effective blood volume inducing circulatory collapse, acute left ventricular failure or acute renal failure. One treatment session may take hours to complete. It also could present certain other risks: heart failure caused by the rapid transfer of blood, blood loss, acute kidney failure due to temporary major depletion of effective circulatin, plasma volume, and/or the possible spreading of dangerous diseases such as HIV, hepatitis B, and hepatitis C. The therapeutic method of the present invention avoids these problems. It merely requires an injection, or other equivalent mode of administration, of an antibody composition to the patient.

High dose intravenous immune globulin (IVIG) infusions have also been used in treating certain autoimmune diseases. Previous studies have indicated that IVIG may contain anti-idiotype activity against anti-DNA antibodies, as well as many other autoantibodies (Jordan, S. C., 1989; Silvestris et al, 1994; Mouthon et al, 1996; Silvestris et al, 1996). The effects of IVIG infusions are apparently related to changes in the repertoire of autoantibodies expressed in the patient. This modulation of pathogenic Id antibodies is thought to depend on their specific interaction with the regulatory anti-idiotype molecules that occur naturally in healthy donors. Production of anti-idiotypic antibodies inhibiting the potentially harmful autoimmune repertoire may result from activation of the Id network committed to controlling the secretion of natural autoantibodies by CD5-positive B cells.

Up until the present time, treatment of SLE with IVIG has provided mixed results, including both resolution of lupus nephritis (Akashi et al, 1990), and in a few instances, exacerbation of proteinuria and kidney damage (Jordan et al, 1989). The cause of this increase is not clear but it is believed that there is increased glomerular deposition of immune-complexed, polyreactive, non-Id-specific IgG antibodies.

As can be understood from the above, although there are several treatments for autoimmune disease such as systemic lupus erythematosus, all possess serious disadvantages. Thus, persons afflicted with SLE who show clinical evidence for SLE nephritis need a cost-efficient and safe treatment that will help prevent or ameliorate the tissue damage that leads ultimately to kidney failure and the need for chronic hemodialysis and/or renal transplantation caused by their condition.

BRIEF SUMMARY OF THE INVENTION

The subject invention concerns novel compositions and methods for the treatment of antibody-based autoimmune diseases, and in particular, SLE. One aspect of the present invention concerns a therapeutic method for treating patients suffering from, or predisposed to, autoimmune disorders such as SLE nephritis. The method comprises administering an anti-idiotypic antibody composition to a patient afflicted with an autoimmune disease, wherein the anti-idiotypic antibodies selectively immunoreact with autoantibodies bearing the appropriate idiotype, thereby inhibiting the autoantibodies and their destructive autoimmune responses without inducing generalized immunosuppression. The novel anti-idiotypic antibody compositions, prepared in accordance with the procedures of the subject invention, comprise anti-idiotypic antibodies having specificity for pathogenic self-reactive antibodies in a patient's body, thereby modulating the potential of the self-reactive antibodies to form immune complexes with self antigens and cause harm to normal cells and tissues, particularly within the patient's kidney filtering systems. One embodiment of the present invention is a method for treating SLE using anti-DNA anti-idiotypic antibody compositions prepared from pooled human intravenous gnmma globulin (IVIG). The potential risks and negative side effects associated with other current autoimmune disease therapies are avoided with the present method.

Another aspect of the subject invention concerns novel compositions comprising purified human anti-idiotypic antibodies which have binding specificity for self-reactive antibodies that are associated with clinical pathogenesis of certain autoimmune diseases. The antibody compositions are capable of modulating the deleterious effect of the self-reactive autoantibodies on cells and tissues of the affected patient. Specifically exemplified in the present invention is a purified anti-DNA anti-idiotypic antibody composition that can be used to treat patients afflicted with SLE nephritis.

In a further aspect, the subject invention is directed toward a method of producing the novel anti-idiotypic antibody compositions which can be used in the therapeutic method of the present invention. The subject antibodies can be produced by adsorbing pooled normal human gamma globulin with a solid phase substrate having antibody molecules attached thereto that selectively bind with anti-idiotypic antibodies present in the human gamma globulin, whereby an antibody/anti-id antibody complex is formed on the solid phase. The anti-idiotypic antibodies from the intravenous gamma globulin preparations are then eluted from the solid phase substrate. The procedure allows for the isolation and enrichment of anti-idiotypic antibodies from the other antibodies present in the pooled ganma globulin preparation.

BRIEF SUMMARY OF FIGURES

FIGS. 1A and 1B show only slight to moderate inhibition (25–50%) of SLE Pop and Bea APAD by anti-DNA Id(+)-column eluates, and no inhibition by column flow-through fractions. In FIGS. 1C and 1D major inhibition (70–100% of SLE APAD McK and Bel was recorded with anti-DNA Id(+)-column eluates. Positive control inhibition of SLE APAD binding by DNA is shown with the curves marked DNA.

FIG. 2 shows a diagrammatic representation of the idiotypic/anti-idiotypic assay system. dsDNA was coated on an ELISA plate and biotinylated affinity purified SLE IgG APAD was pre-incubated with a broad range of concentrations of anti-DNA Id(+) column eluate (dotted line antibodies). However, since anti-DNA Id(+) column eluate antibodies themselves have anti-DNA reactivity, apparent inhibition shown by a singe * might be observed if anti-DNA Id(+) column eluates take up a significant fraction of the antigenic sites on ELISA plate DNA (double asteriks**).

DETAILED DESCRIPTION OF THE INVENTION

The subject invention concerns a novel therapeutic method that can be used to beneficially treat persons afflicted with autoimmune disorders. The treatment procedures of the subject invention represent an important advance in the care of patients suffering from, or predisposed to, autoimmune disorders, such as SLE nephritis. These disorders are a disparate collection of human diseases that have in common the failure of the immune system to recognize a tissue, organ or cellular component of the body as self. As the result of these pathological processes, a person's own ceUs and tissues are targeted for attack by their immune system. Specifically exemplified herein is a treatment procedure to alleviate the destructive effects of SLE on the kidney. Other diseases that can be treated according to the present invention include, for example, myasthenia gravis, idiopathic thrombocytopenic purpura, and HIV infection.

As used herein, the term "anti-DNA antibodies" refers to antibodies that have specificity for double-stranded or native DNA.

As used herein, the term "anti-DNA idiotype (+)" and "anti-DNA Id(+)" refer to anti-DNA antibodies that have been typed positive for the expression of idiotypic determinants associated with anti-DNA antibodies.

As used herein, the term "anti-DNA anti-idiotypic antibodies" refers to anti-idiotypic antibodies that have specificity for idiotypic determinants associated with anti-DNA antibodies.

The present therapeutic method comprises administering to a patient in need of treatment an effective amount of an anti-idiotypic antibody composition, or antigen binding fragments thereof, which can bind to and inhibit self-reactive autoantibodies present in the patient. One embodiment of the therapeutic method of the present invention to treat persons diagnosed with, or predisposed to, SLE utilizes anti-DNA anti-idiotypic antibodies, or antigen binding fragments thereof, produced from pooled gamma globulin of normal individuals. The method comprises administering to the patient an effective amount of an anti-DNA anti-idiotypic antibody composition that has binding specificity for pathogenic self-reactive anti-DNA autoantibodies produced by and present in the patient's body. In a preferred embodiment, the anti-idiotypic ant-body composition comprises human antibodies.

The anti-DNA anti.idiotypic antibody composition is preferably administered to a person intravenously. Therapeutic application of the antibody composition can be accomplished by any suitable therapeutic method and technique presently or prospectively known to those skilled in the art. The anti-DNA anti-idiotypic antibody composition can be administered in any suitable solution, such as, for example, a dextrose saline solution. The amount of antibody composition to be administered, as well as the number of treatments a patient receives, can be determined by clinicians skilled in the art. Typically, a patient will receive multiple treatments over time. Materials used in the present treatment method can be sterilized according to conventional means.

Administration of human-specific anti-idiotypic antibody to SLE patients may be able to produce a lasting or prolonged down-modulating effect on the hyperactive immune reactions present in the SLE patient's immune system. The anti-DNA anti-idiotypic antibodies interfere with the ability of self-reactive anti-DNA antibodies to immunoreact with, and thereby damage, a person's own tissue and cells. The therapeutic administration of anti-DNA anti-idiotypic antibodies results in a significant decrease in the amount of anti-DNA antibodies present in the body of a SLE patient, and reduces the amount of tissue damage in the kidneys.

Unlike previous treatments for SLE using a general nonspecific pool of commercial gamma globulins, the therapeutic method of the present invention is less likely to exacerbate the problem of tissue damage or trigger an increased autoimmune response in the treated patient since the antibody composition administered according to the subject invention has been treated in a manner such that substantially only antibodies that immunoreact with idiotypes present on anti-DNA antibodies remain in the therapeutic composition. Thus, the method of the subject invention overcomes the problems associated with previous treatments, e.g., tissue damage caused by glomerular deposition of immune-complexed, polvreactive, non-anti-DNA Id-specific immunoglobulins.

The mechanism of action of the subject method is highly selective and only counteracts the adverse effects of destructive antibodies already present in the body of the SLE-afflicted patient. No other component of the immune system, albeit humoral or cellular, is disrupted. Thus, the patient's immune system is not significantly weakened, unlike those treatment methods where immunosuppressant drugs are used to treat certain autoimmune disorders.

The present invention also concerns a method for producing a composition that is highly enriched for anti-idiotypic antibodies or antigen binding fragments thereof, from a pool of gamma globulin, whereby the anti-idiotypic antibodies are reactive with idiotypes present on antibodies that are associated with certain autoimmune disorders. In a preferred embodiment, the subject method comprises contacting pooled, normal human gamma globulin with a solid phase substrate comprising antibodies that express idiotypic determinants of DNA-reactive antibodies (i.e., anti-DNA Id(+)), resulting in the formation of an idiotypic/anti-idiotypic antibody complex on the solid phase substrate, and then eluting the adsorbed anti-DNA anti-idiotypic antibodies from the substrate. The adsorbed antibodies can be eluted using methods and materials known in the art, such as, for example, a low pH buffer. The substrate having the adsorbed antibodies present thereon may be washed with a suitable wash buffer prior to elution.

The solid phase substrate can include, but is not limited to, any structural component commonly known in the art that is suitable for such purpose, such as DEAE, Sepharose, glass beads, PVDF, nitrocellulose and plastics such as polystrene. The molecules expressing the idiotypic markers of interest can be coupled to the solid phase substrate by means known in the art. In a preferred embodiment, anti-DNA antibodies coupled to the support matrix comprise human IgG that possess at least one of the following idiotypic markers: 16/6, F4, 3I, and 8.12. Other anti-DNA antibodies expressing idiotype markers are known in the art and can be used in accordance with the subject invention.

Idiotypic structural and conformational determinants associated with a self-reactive autoantibody, such as, for example, anti-DNA antibodies, for use with the present invention can also be prepared using hydropathic analysis of primary variable region amino acid sequences of the antibodies, followed by construction of synthetic peptides capable of duplicating these idiotypic determinants (Blalock, 1990; Maier et al, 1994). These synthetic peptides can also be coupled to a solid phase substrate and used to purity anti-idiotypic antibodies from pooled gamma globulin or other fluids. Accordingly, these peptides are contemplated within the scope of the present methods.

The subject invention further concerns novel antibody compositions that can be used to treat patients suffering from autoirnrnune disorders, such as SLE, according to the therapeutic methods described herein. An antibody composition of the invention comprises anti-idiotypic antibodies that selectively bind to antibodies bearing idiotypes associated with pathogenic self-reactive autoantibodies of the patient afflicted with the autoirrune disorder. Preferably, the anti-idiotypic antibodies are isolated and enriched from a pool of normal human gamma globulin. In a preferred embodiment useful for treating SLE, the antibody composition is composed of purified anti-DNA anti-idiotypic antibodies which bind to self-reactive anti-DNA antibodies. Preferably, the anti-DNA anti-idiotypic antibodies bind specifically to those antibodies that are specific for native double-stranded DNA. The anti-idiotypic antibody composition specifically exemplified herein has binding specificity for the following human idiotypic markers present on anti-DNA antibodies: 16/6, F4, 3I, and 8.12. However, antibodies with specificity for idiotype markers of anti-DNA antibodies other than those specificaly exemplified herein can be prepared and isolated by the ordinarily skilled artisan using the teachings contained herein, and are contemplated within the scope of the present invention.

The antibody composition of the present invention can also be used to detect the presence of self-reactive autoantibodies, such as anti-DNA antibodies, in a sample, such as a biological fluid, using methods well known in the art. For example, the antibody composition of the invention can be used in radioimmunoassays (RIA) and enzyme-linked immunosorbet assays (ELISA). Typically, the subject antibody composition is contacted with a sample suspected of having self-reactive autoantibody therein that is immunoreacts with the subject antibody. After contacting the sample and allowing antibody binding to occur, bound antibody is detected using standard techniques. The amount of autoantibody present in the sample can be quantified using methods well known in the art.

Also included within the scope of the present invention are antigen binding fragments of whole antibody, wherein the fragments retain the binding specificity of the whole antibody molecule. These binding fragments include, for example, Fab, F(ab')$_2$, and Fv fragments. Binding fragments can be obtained using conventional techniques, such as proteolytic digestion of antibody by papsin or pepsin, or through standard genetic engineering techniques that are well known in the art.

The subject invention also concerns kits comprising in one or more containers a purified anti-idiotypic antibody composition that has binding specificity for self-reactive autoantibodies. In a preferred embodiment, the anti-idiotypic antibody composition of the kit comprises human anti-DNA anti-idiotypic antibodies.

Materials and Methods
Preparation of Anti-DNA Idiotype Antibody Coupied Substrate Three hundred human IaG myeloma proteins were typed for four different anti-DNA idiotypic markers (16/6, F4, 3I, and 8.12) as previously described (Williams, Jr. et al., 1994). Originally, all 300 IgG myelomas were selected on the basis of their cationic electrophoretic behavior because of the known proclivity of naturally occurring anti-DNA reactivty in human SLE and murine SLE models to be associated with cationic IgG molecules (Gauthier et al, 1982; Ebling et al., 1980; Gallo et al., 1981). A panel of these human IgG myelomas possessing at least one or several of the four previously characterized anti-DNA idiotypic markers referred to herein as 16/6, F4, 3I, and 8.12 (Shoeneld et al., 1989; Halpern et al., 1984; Davidson et al., 1989; Davidson et al., 1990) were isolated by diethylaminoethyl cellulose (DEAE) chromatography, cross absorbed with insoluble Sepharose 4B immunoabsorbents linked to opposite light chain type goat anti-human Kappa or lambda chain antibodies by cyanogen bromide coupling (Williams, Jr. et al., 1994), and then lnked to Sepharose 4B to provide an immnunoabsorbent column representing human IgG molecules bearing antigens similar to or encompassing parts of the respective anti-DNA 16/6, F4, 3I, and 8.12 idiotypic markers. 10 mg of anti-DNA idiotype(+) myeloma protein was used per gram of Sepharose 4B to couple the myeloma proteins to the Sepharose solid phase substrate. After subsequent extensive washings of the Sepharose 4B coupled with the anti-DNA idiotype(+) myelomas (Sepharose/anti-DNA idiotype(+)column), no human gamma globulins were detected in column washings using a sensitive ELISA assay.

Several controls were included in the series of experiments involving the Sepharose/anti-DNA idiotype(+) column. Two additional Sepharose/myeloma columns were prepared as controls. One column consisted of four cationic human IgG myelomas that lacked intrinsic anti-DNA activity and that also lacked positive reactions for the four anti-DNA idiotypes markers (F4, 3I, 16/6, and 8.12). A second control column consisted of four strongly anionic IgG myelomas, which were also negative by ELISA for anti-DNA antibody activity and negative for each of the anti-DNA idiotype markers. Pooled human intravenous gamma globulin preparations were adsorbed and eluted from these control Sepharoselmyeloma columns in parallel.

Three different preparations of intravenous gamma globulins were selected for study and are identified herein as lots P-3, L-2, and M-1. Each gamma globulin lot represented highly purified human IgG from an estimated pool of 25,000 to 35,000 individual donors. The P-3, L-2, and M-1 lots were chosen for study since they respectively represented relatively high (O.D. 1.760), medium (O.D. 0.396), and very low (O.D. 0.017) levels of generic anti-idiotype IgG anti-F (ab')$_2$ (Williams, Jr. et al., 1995a; Williams, Jr. et al., 1995b). Gamma globulin from lot P-3, L-2, or M-1 was applied at room temperature to a Sepharose/human anti-DNA idiotype (+) myeloma column as a solution of 10–20 mg/ml protein in 0.1 M phosphate-buffered saline (pH 7.4) (PBS) and allowed to adsorb to the column at room temperature for several minutes before washing the columns using 0.1 M PBS. The column was then eluted with 0.1 M pH 2.5 glycine-saline buffer and the eluates immediately brought to neutral pH (about 7.4) with Tris. Subsequent testing of low pH glycine-saline eluted columns using chaotropic buffers (thiocyanate or cacodylate) did not produce any additional elution of column-adherent IgG, indicating that the glycine-saline elution procedure was relatively efficient.

After the gamma globulin-adsorbed Sepharose/anti-DNAidiotype(+) myeloma columns were eluted and the eluates brought to neutral pH, all eluates were adjusted to a protein concentration of 5 mg/ml and tested for their ability to inhibit binding of affinity purified biotinylated anti-DNA IgG antibodies (APAD) obtained from a representative panel of patients with active SLE. Affinity purified anti-DNA antibody from four patients with active SLE nephritis (established by biopsy) and four other patients with active severe central nervous system (CNS) involvement and high anti-DNA antibody titers were chosen for evaluation. The four SLE patients with CNS involvement showed no clinical evidence for concomitant renal disease (normal urinalysis and normal serum creatinine and BUN). Affinity purified anti-DNA IgG antibody was prepared from the serum or plasma of SLE patients using DEAE cellulose chromatography (0.01 sodium, potassium phosphate buffer pH 7.0) to purify the IgG fraction from the serum or plasma. The IgG was then concentrated to about 5–10 mg/ml and applied to a DNA-coupled Sepharose affinity column at neutral pH (pH 7.4). After thorough washing of the affinity column, adherent IgG that had bound to the DNA was eluted at pH 2.5 with 0.1 M glycine-saline buffer. Eluates were immediately brought to neutral pH 7.4 with Tris. The purified anti-DNA.IgG preparations were then biotinylated using standard procedure as described in (Bayer et al., 1980). Biotinylated affinity purified anti-DNA IgG antibody that iinunoreacted with DNA by ELISA was used to measure anti-DNA antibody binding to DNA. ELISA assays of affinity purified anti-DNA IgG binding to DNA on the ELISA plate before and after biotinvlation showed that the biotinylation procedure did not affect the anti-DNA reactivity of the original affinity purified anti-DNA IgG. lnhtbition of biotinylated SLE affinity purified anti-DNA antibody reacting with DNA on the ELISA plates was estimated by preincubation of a standard amount of SLE biotinylated affinity purified anti-DNAantibody with either the anti-DNA idiotype(+) myeloma column eluates (E) or flow-through (FT) materials at room temperature for 30 minutes. The respective eluates and flow-through fractions were tested for inhibition of affinity purified anti-DNA antibody reacting with DNA by ELISA using a broad nanomolar concentration range of either anti-DNA idiotype(+) column eluate or flow-through fractions. Biotinylated SLE affinity purified anti-DNA antibody from nephritis or cerebritis patients was tested using equal amounts of anti-DNA activity as initially tested in the ELISA assays.

Assays of Anti-DNA Idiotype Myeloma Column Eluates and Flow-through Fractions for Anti-DNA and Anti-F(ab'), Specificities All anti-DNA idiotype(+) myeloma affinity column eluates and flow-through fractions prepared from pooled human gamma globulin preparations were tested for both anti-DNA as well as anti-F(ab')$_2$, anti-Sm and anti-RNP activity using ELISA assays as previously described (Silvestris et al., 1984; Williams, Jr. et al., 1995a; Williams, Jr. et al., 1995b; Williams, Jr. et al., 1995c). The anti-DNA ELISA assay employed showed that liquid phase DNA inhibited the binding of anti-double stranded DNA to the plates. Liquid phase inhibition of anti-Sm or anti-Sm/RNP was demonstrated for Sm or Sm/RNP antigen, respectively, as well. In addition, column eluates and flow-through materials were also tested for conventional rheumatoid factor (RF) activity using Fc or rabbit IgG coated on ELISA plates at 5 mg/ml, and developed with peroxidase-conjugated goat F(ab')$_2$ anti-human light chain developing reagent. Assays of ELISA reactivity with Sm and RNP antigen (Immunovision, Springdale, Ark.) were performed as previously described (Williams, Jr. et al., 1995C).

Measurement of Antibody Affinity

Individual antibody population affinities were also measured using an ELISA inhibition method originally described by Devey et al. (1988) with proper attention to pH effects as emphasized by Goldblatt et al. (1993). This method employs an ELISA assay in which diethylamine (DEA) is employed as a chaotropic agent by which functional unities of antibodies to complex antigens can be determined and compared. The method is based on determining the leftward shift of a dose-response curve for antibody reacting with antigen coated on the ELISA plate after introduction of DEA at a pre-established optimal concentration. Affinity was expressed as the mean shift ($\log_{10}$), and the lower the value, the higher was the actual functional affinity.

Following are examples which illustrate materials, methods and procedures, including the best mode, for practicing the invention. These examples are for illustrative purposes only and are not to be construed as limiting.

EXAMPLE 1

Preparation of Anti-DNA Anti-idiotypic Antibody Composition

Figure 1A:
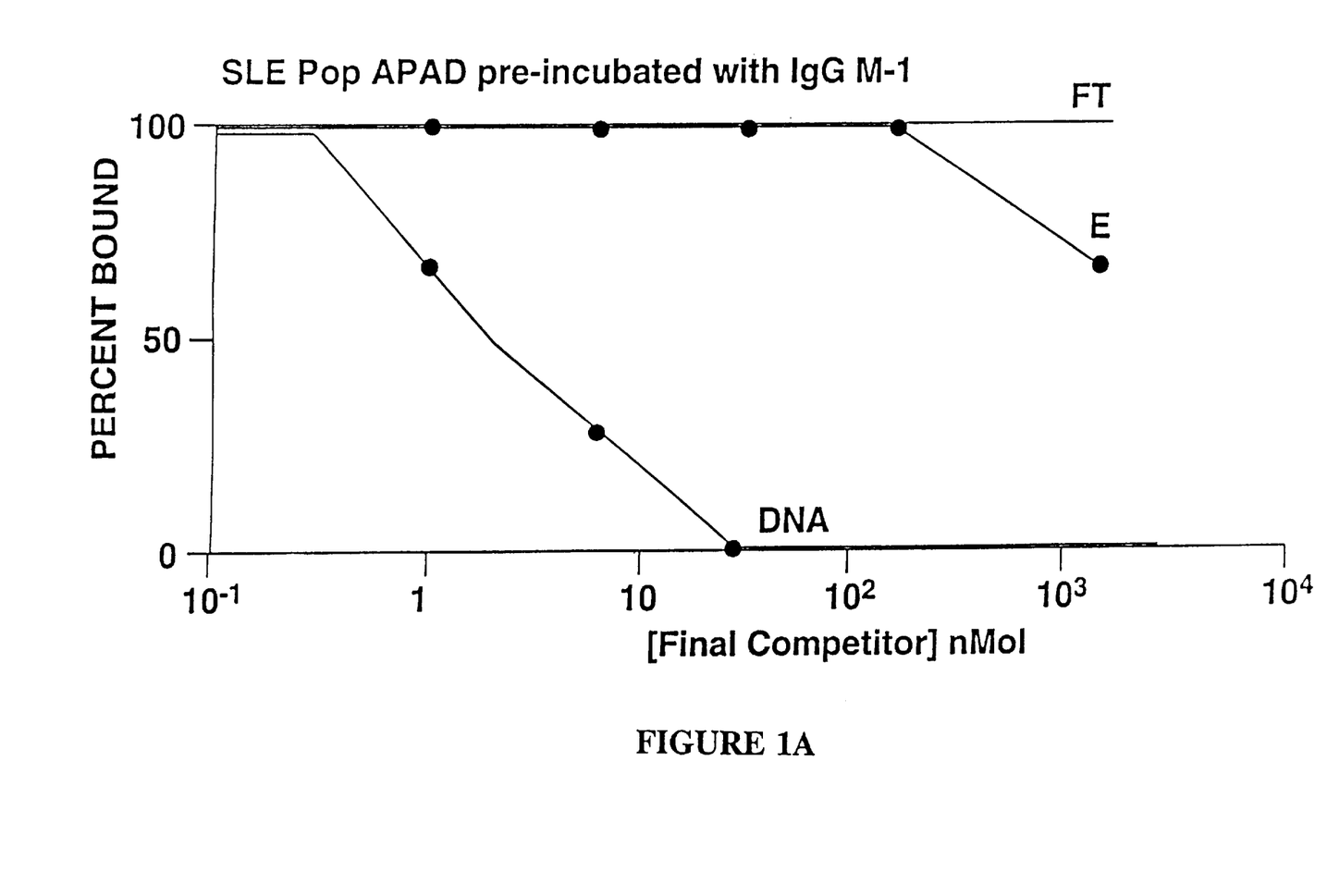
FIGS. 1A–1D show a series of competitive inhibition experiments in which biotinylated SLE affinity-purified anti-DNA IgG antibodies (APAD) was pre-incubated with either flow-through (FT) or eluates (E) from anti-DNA Id(+) monoclonal antibody-coupled affinity columns. A broad nanomolar range of concentrations of inhibiting column eluates or flow-through fractions were then tested with the individual biotinylated SLE APAD preparations.
Figure 1B:
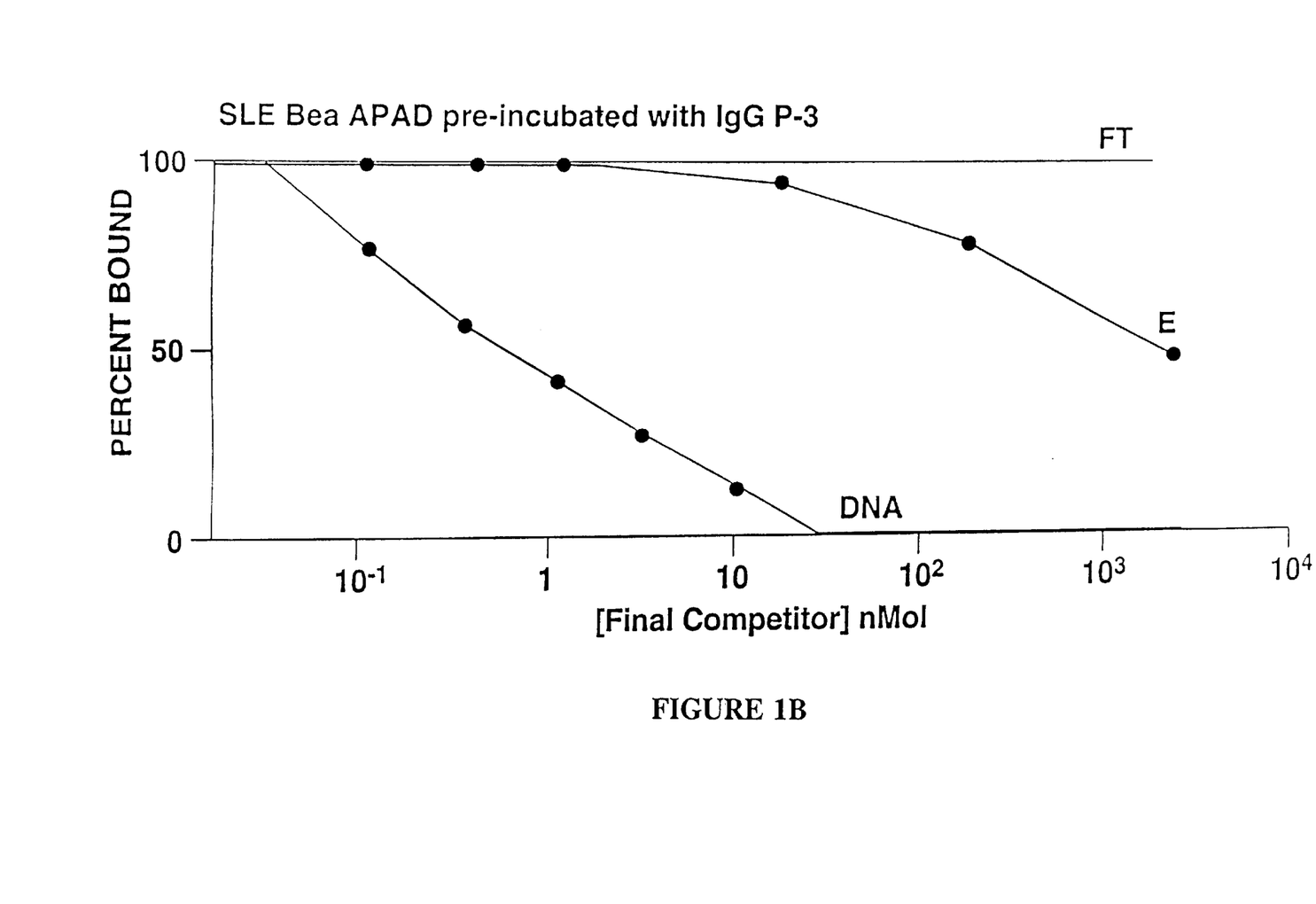
Figure 1C:
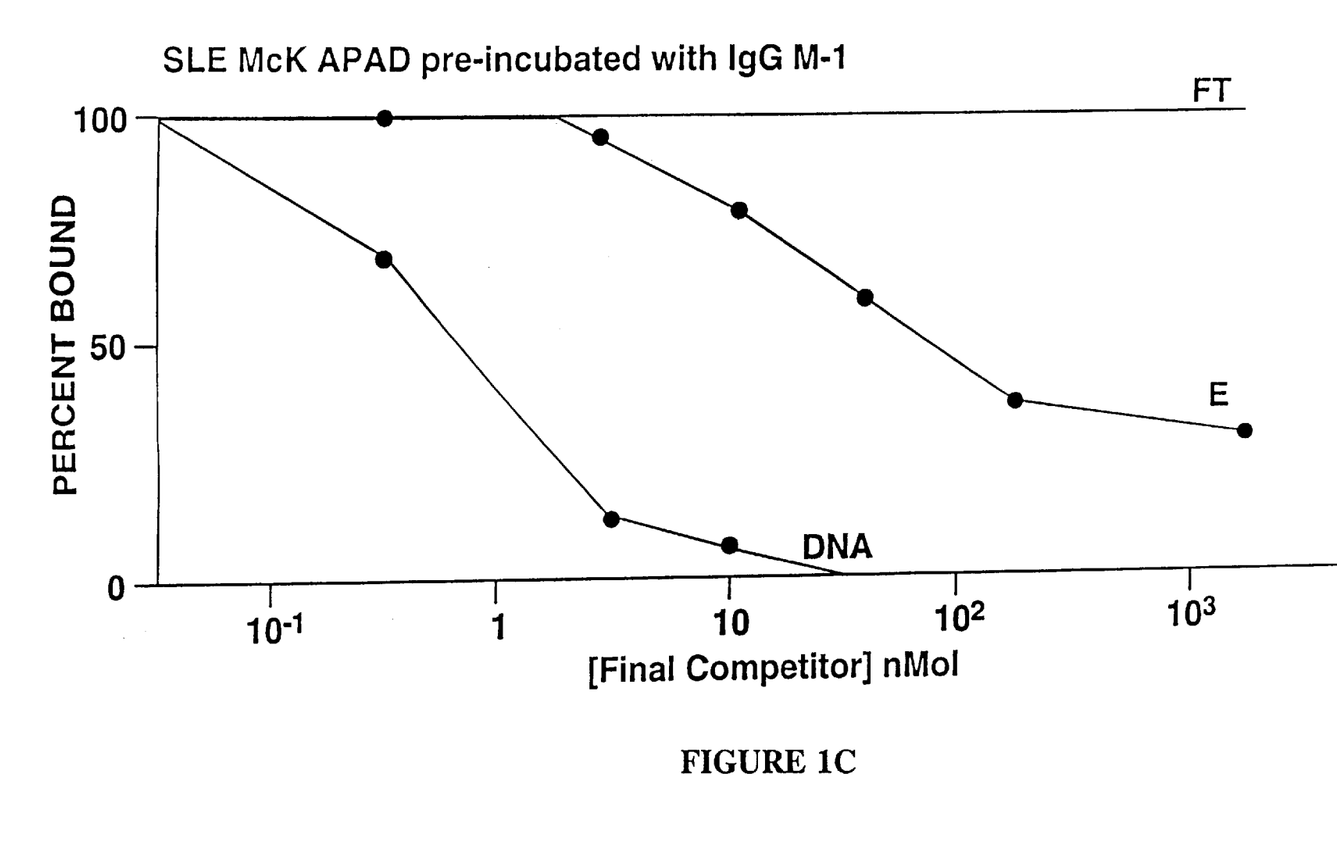
Figure 1D:
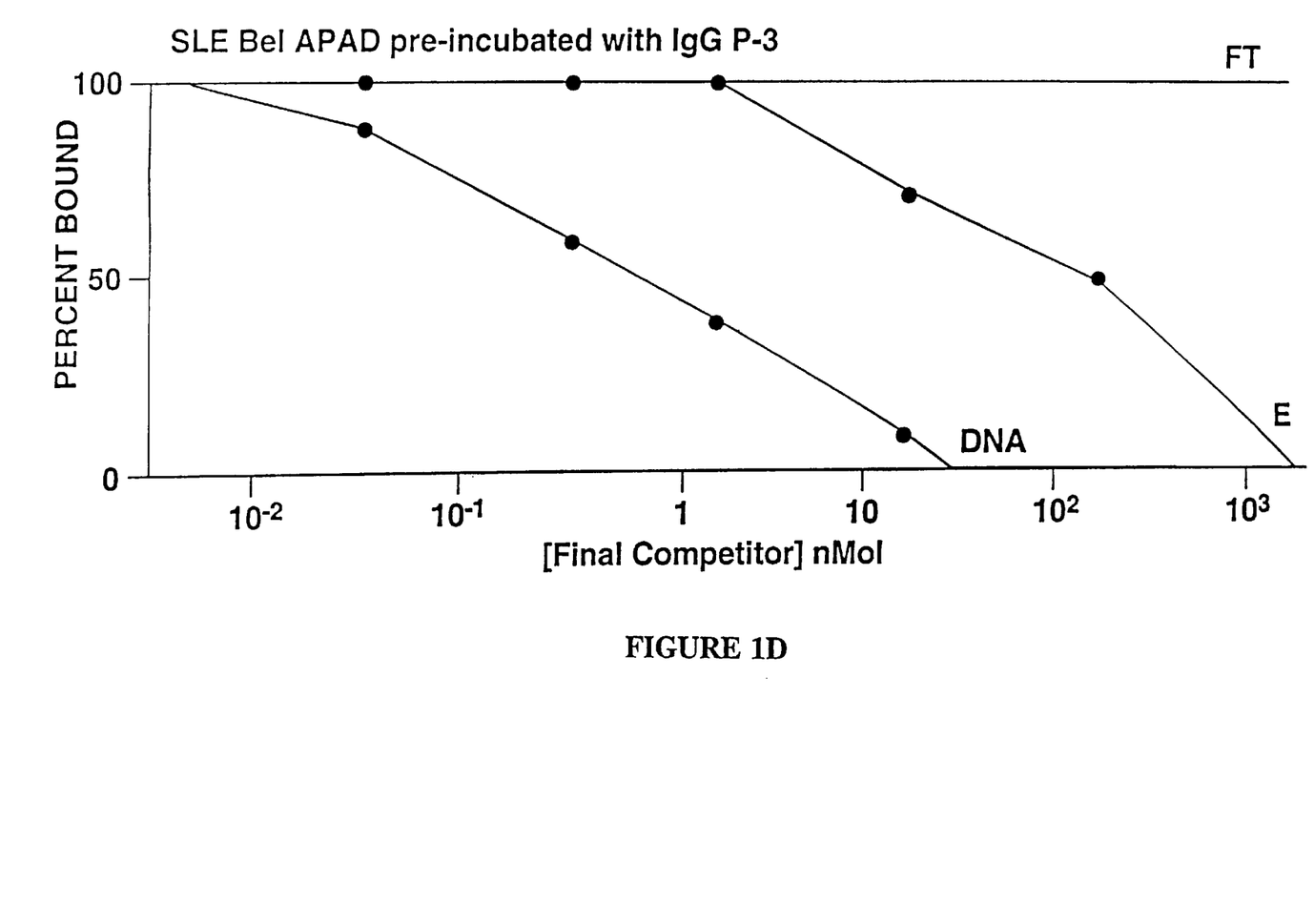

Three different intravenous gamma globulin preparations (P3, L-2, and M-1) were adsorbed to the Sepharose/anti-DNA idiotype(+) human myeloma affinity columns as described in the material and methods section. Most of the gamma globulin in the solution did not adsorb to the column but passed through the column and remained in the flow-through fractions. However, a small proportion (0.04–0.9%) of the original gamma globulin did adsorb to the affinity columns. When the adsorbed fraction was subsequently eluted from the column at low pH, tests for anti-DNA anti-idiotype activity in such myeloma column eluates often showed potent inhibition of biotinylated SLE affinity purified anti-DNA antibody reacting with DNA on the ELISA plate. Thus, in several instances biotinylated affinity purified anti-DNA antibody from SLE patients reacting with DNA by ELISA showed complete inhibition at higher nanomolar concentrations of the anti-DNA idiotype(+) column eluates. By contrast, in no instances did column flow-through fractions show inhibition of affinity purified anti-DNA antibody binding to DNA as measured by ELISA. Although gamma globulin lots with high baseline anti-F(ab')$_2$ activity frequently showed anti-DNA idiotype(+) column eluates with strong blocking activity for several SLE affinity purified anti-DNA IgG preparations, no clear correlation between anti-F(ab')$_2$ activity and column eluted anti-DNA anti-idiotype (anti-combining site) activity was observed. Thus, in some instances eluates from gamma globulin lots with low anti-F(ab')$_2$ activity showed strong paratope (combining site) inhibition of affinity purified anti-DNA antibodies from SLE patients. Examples of these results are shown in FIGS. 1A and 1B. A summary of the affinity purified anti-DNA antibody inhibition results obtained with eight different SLE patients is shown in Table 1.

TABLE 1

Relative degrees of Inhibition of Biotinylated SLE APAD reacting with DNA on ELISA plates by a broad nanomolar range of 3 different preparations of IVIG (Baxter)

| SLE APAD* | High anti-F(ab')$_2$ P3 Nanomolar[+] | | | Intermediate anti-F(ab')$_2$ L2 Nanomolar | | | Low anti-F(ab')$_2$ M-1 Nanomolar | | |
|---|---|---|---|---|---|---|---|---|---|
| Tested | 10 | $10^2$ | $10^3$ | 10 | $10^2$ | $10^3$ | 10 | $10^2$ | $10^3$ |
| Nephritis | | | | | | | | | |
| McK | 25** | 45 | 80 | 16 | 54 | 75 | 20 | 55 | 70 |
| Lar | 15 | 35 | 80 | 20 | 40 | 95 | 42 | 50 | 100 |
| McN | 0 | 10 | 45 | 26 | 50 | 87 | 8 | 20 | 78 |
| War | 12 | 30 | 58 | 0 | 4 | 25 | 0 | 0 | 38 |
| Mean | 13 | 30 | 66 | 15 | 37 | 70 | 18 | 31 | 72 |
| CNS | | | | | | | | | |
| Pop | 0 | 0 | 15 | 16 | 34 | 66 | 0 | 0 | 25 |
| Bel | 20 | 47 | 90 | 0 | 28 | 70 | 0 | 4 | 58 |
| Bea | 5 | 18 | 42 | 0 | 2 | 20 | 0 | 2 | 20 |
| Mor | 0 | 10 | 50 | 4 | 8 | 45 | 0 | 0 | 38 |
| Mean | 6 | 19 | 49 | 5 | 18 | 50 | 0 | 2 | 35 |

[+]Nanomolar concentrations of intravenous gamma globulins P3, L2, or M1 tested in inhibition as eluates from IgG affinity column constructed of 4 human IgG myeloma proteins bearing four different anti-DNA idiotypic markers (F4, 31, 8.12, and 16/6).
*SLE APAD refers to IgG affinity isolated eluates from Sepharose 4B/DNA columns obtained from 8 different SLE patients with active disease (McK, Lar, McN, and War have active SLE glomerulonephritis; Pop, Bel, Bea, and Mor have active SLE central nervous system involvement, but no clinical evidence for renal involvement.
**Numbers refer to percent inhibition of SLE IgG affinity isolated anti-DNA antibody (APAD) reacting with DNA on ELISA plate by IV gamma globulin anti-DNA Id-column eluates tested by preincubation with 10, $10^2$, and $10^3$ nanomolar concentrations.

In general, biotinylated affinity purified anti-DNA antibody from patients with active SLE nephritis showed more inhibition by anti-DNA idiotype(+) myeloma column eluates than was observed with biotinylated affinity purified anti-DNA antibody isolated from the four patients with active central nervous system lupus (Table 1). Parallel control studies with cationic and anionic myeloma-affinity columns all without expression of any of the four major anti-DNA idiotype markers (16/6, F4, 3I, or 8.12) showed that quantitative amounts of gamma globulin which actually adsorbed to such columns were less than one quarter to one eighth the amounts adsorbed from the same lots of P-3, L-2, or M-1 gamma globulin. Moreover, none of the eluates of flow through fractions from such control anti-DNA idiotpe-negative cationic or anionic myeloma affinity columns showed any significant inhibition in the biotinylated SLE affinity purified anti-DNA antibody experiments similar to those illustrated in FIGS. 1A–D or in Table 1. These results suggest that in order to concentrate functional anti-DNA anti-idiotype reactivity from gamma globulin preparations capable of blocking individual SLE anti-DNA antibody it was necessary to adsorb such preparations on cationic anti-DNA idiotypic(+) myeloma immunoadsorbents rather than merely pooled cationic myelomas alone.

EXAMPLE 2

Anti-DNA Antibody, Anti-F(ab')$_2$, anti-Sm and Anti-RNP Antibody Activity in Anti-DNA Idiotyuic(+) column Eluates and Flow-through Fractions Column eluates of gamma globulin which had adhered to Sepharose/anti-DNA idiotype(+) myeloma affinity columns were studied in parallel with flow-through fractions for intrinsic anti-DNA as well as anti-F(ab')$_2$ and anti-Sm or anti-Sm/RNP activity by ELISA. Thus, myeloma anti-DNA idiotype(+) column eluates from all three lots of gamma globulin (P-3, L-2, and M-1) showed considerable relative concentration of anti-DNA activity compared with activity in the starting lots of gamma globulin studied at the same IgG concentrations (see Table 2).

TABLE 2

ELISA reactions of intravenous gamma globulin preparations P3 and L2 before and after adsorption to anti-DNA Id(+) human IgG myeloma column

| Intravenous gamma globulin preparation | ELISA Anti-DNA | Anti- F(ab')$_2$ | Anti-Sm | Anti-RNP |
|---|---|---|---|---|
| IVIG P3 untreated | 0.521* | 1.760+ | 0.235+ | 0.276+ |
| IVIG P3 over anti-Id + column (flow through fraction) | 0.193 | 0.105 | 0.287 | 0.353 |
| P3 Eluate from anti-Id + human myeloma column | 1.704 | 1.400 | 1.054 | 2.194 |
| IVIG L2 | 0.585* | 0.396 | 0.161 | 0.215 |
| IVIG L2 over anti-Id + column (flow through fraction) | 0.616 | 0.064 | 0.148 | 0.214 |
| L2 Eluate from anti-Id + column | 0.937 | 1.049 | 0.547 | 0.719 |

*ELISA anti-DNA activity of each intravenous preparation studied at 5 μg/ml with dsDNA (2.5 μg/ml) coated on ELISA plate.
+anti-F(ab')$_2$, anti-Sm, and anti-RNP determined by standard ELISA with F(ab')$_2$ 5 μg/ml and Sm and RNP 20 u/ml on ELISA plate.

Gamma globulin from lot P3 showed 0.521 OD anti-DNA reactivity composed with only 0.193 OD for the flow-through fraction. The P3 low pH eluate produced a 1.704 OD in the anti-DNA ELISA assay. In parallel, the unadsorbed gamma globulin lot P3 showed relatively high anti-F(ab')$_2$ with little residual anti-F(ab')$_2$ in flow-through fractions, and again high anti-F(ab')$_2$ activity in the anti-DNA idiotype(+) column eluate. Although baseline gamma globulin lot P3 showed low ELISA values for anti-Sm and anti-RNP activity, low pH anti-DNA idiotype(+) column eluates showed marked relative concentration of each of these antibody activities as well. A similar profile was noted with gamma globulin M-1 before and after adsorption on the anti-DNA idiotype(+) myeloma affinity column.

When similar adsorption studies of the same three gamma globulin preparations were performed using the anti-DNA idiotypic-negative cationic and anionic myeloma affinity columns, no marked relative increments in anti-DNA or anti-F(ab')$_2$, anti-Sm, or Sm/RNP were recorded in column eluates with respect to flow-through fractions or original starting material. These findings confirmed the fundamental importance of using cationic myeloma proteins which were positive for several common anti-DNA idiotypic markers.

Figure 2:
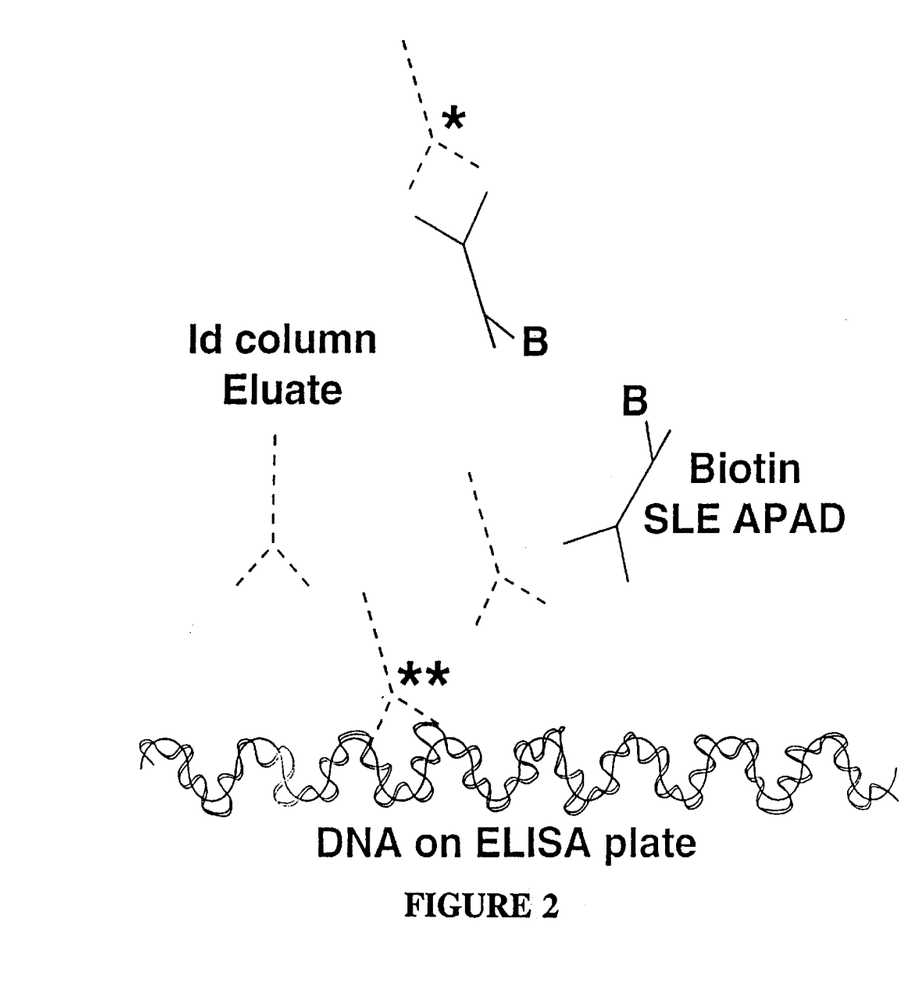
Figure 3:
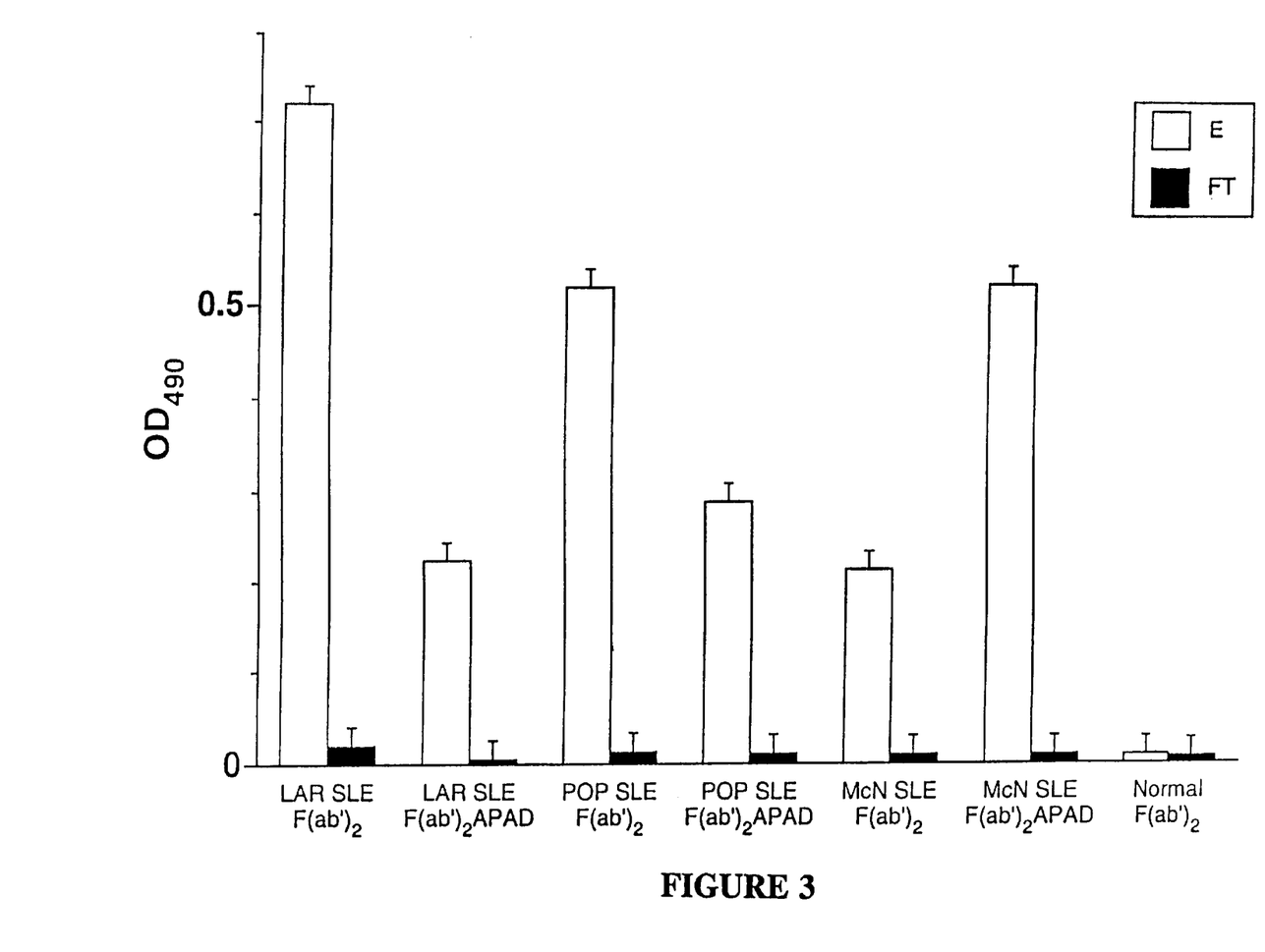
FIG. 3 shows ELISA activities of anti-DNA Id(+) column eluates (E) and flow-throuah fractions (FT) with SLE IcG F(ab')$_2$ as well as specifically purified F(ab')$_2$ fragments of affinity purified SLE IgG anti-DNA F(ab')$_2$ (APAD F(ab')2) in comparison to reaction with normal subjects' IgG F(ab')$_2$. Much stronger reactions were recorded with both whole SLE F(ab')$_2$ and annnity purified F(ab')$_2$ of SLE anti-DNA and anti-DNA Id(+) column eluates than with column flow-through fractions. No ELISA reaction was noted with IgG F(ab'), from 10 normal subjects.

Since gamma globulin anti-DNA idiotype(+) column eluates could be demonstrated to contain a relative increase in anti-DNA reactivity over and above that present in the starting gamma globulin preparations, it seemed possible that preincubation of test SLE biotinylated affinity purified anti-DNA antibody with anti-DNA idiotype(+) column eluates which resulted in inhibition of biotinylated SLE affinity purified anti-DNA antibody binding to DNA as determined by the ELISA might reflect competition for DNA binding between the biotinylated SLE affinity purified anti-DNA antibody and the anti-DNA idiotype(+) column eluate (see FIG. 2). In order to examine this question directly, anti-DNA idiotype(+) column eluates and flow-through fractions were compared for their intrinsic binding activity against IgG F(ab')$_2$ fragments of normal subjects and SLE patients' IgG in parallel with their binding for F(ab')$_2$ fragments of SLE affinity purified anti-DNA antibody. As shown in FIG. 3, these experiments clearly showed that anti-DNA idiotype(+) column eluates (but not flow-through fractions) showed marked relative binding to both IgG F(ab')$_2$ from SLE patients and F(ab')$_2$ fragments of SLE affinity purified anti-DNA antibody, but very little binding to F(ab')$_2$ from individual normal subjects. FIG. 3 shows that in one instance, eluates showed stronger reactivity for F(ab')$_2$ of SLE affinity purified anti-DNA antibody than merely whole SLE IgG F(ab')$_2$ fragments. Such results support apparent marked anti-DNA idiotype specificity within eluate fractions for antigenic determinants on variable regions (and presumably combining sites) of specifically purified SLE anti-DNA antibodies.

Relative affinities of anti-DNA idiotypic(+) column eluates for DNA were measured using the DEA dissociation ELISA inhibition method (Devey et al., 1988) and compared to relative affinities of a broad panel of affinity purified anti-DNA IgG antibodies from SLE patients. Representative data are shown in Table 3.

TABLE 3

Relative functional affinity of anti-DNA Id(+) myeloma affinity columm eluates for DNA in parallel with anti-DNA affinity of SLE patients APAD

| Samples Tested | | $Log_{10}$ conc at 50% Max OD | $Log_{10}$ conc with 25 mM DEA at 50% Max | $Log_{10}$ Shift at 50% Max |
|---|---|---|---|---|
| IVIG P-3 | Id-column eluate | 1.88 | 1.13 | 0.75* |
| IVIG L-2 | Id column eluate | 1.93 | 1.21 | 0.72 |
| IVIG M-1 | Id column eluate | 1.52 | 0.54 | 0.98 |
| SLE IgG | APAD McN** | 1.43 | 1.02 | 0.41 |
| SLE IgG | APAD Ag | 1.53 | 1.08 | 0.45 |
| SLE IgG | APAD Op | 1.76 | 1.67 | 0.09 |
| SLE IgG | APAD Gio | 1.51 | 1.23 | 0.15 |
| SLE IgG | APAD Dan | 1.51 | 1.32 | 0.37 |

*Affinity expressed as $Log_{10}$ shift; numbers indicate relative affinities for DNA. The lower the number, the higher is the test antibody affinity.
**APAD refers to IgG affinity purified anti-DNA antibody obtained by low pH elution from a DNA-Sepharose 4B column.

In all instances, affinity for DNA was higher in affinity purified anti-DNA antibody preparations from SLE patients than was recorded with anti-DNA idiotypic(+) column eluates adsorbed with lots P-3, L-1, or M-1. These findings indicate a much higher DNA affinity within SLE patients' circulating anti-DNA IgG antibody than with the anti-DNA idiotypic(+) column eluates.

EXAMPLE 3

Treatment and Evaluation of SLE Patients

Patients with established SLE who meet ARA (American Rheumatism Association) criteria for definite SLE and who show clearcut clinical and laboratory evidence of SLE nephritis will be selected for treatment. Most patients will have had their SLE nephritis previously confirmed and documented with a recent kidney biopsy. Patients will typically receive intravenous anti-DNA anti-idiotypic antibody preparations prepared as described herein once every six weeks for a total of five treatments. At each visit they will have routine urinalysis and blood drawn for anti-nuclear antibody, anti-DNA, and anti-F(ab')$_2$ determinations. At the beginning of the study, and after the third and fifth treatment, 24 hour urines and blood will be collected for 24 hour urine protein excretion and creatinine clearance determination. Six weeks following the completion of the course of therapy and again three months following completion of the treatment protocol, all patients will be re-evaluated in clinic with CBC, urine, chemistry profile, ANA, anti-DNA and 24 hour urine for protein and creatinine clearance to re-assess stability of their overall condition and renal function.

Anti-DNA anti-idiotypic antibody compositions can be administered as 150 mg of IVIG in a running solution of 5% Dextrose in saline over a period of 1–2 hours. This is similar to the current recommended protocol of regular IVIG administration where a much larger total amount and concentration (400 mg/Kg or 28 grams for a 70 Kg individual) is usually given. The usual starting rate of IV administration is 0.5 ml/Kg hr of a 5% gamma globulin solution increasing over one hour to 4 ml/Kg/hr. The same general protocol for IVIG can be followed with the present method; thus, the total of 150 mg of the anti-DNA anti-idiotypic antibody composition can be infused as a 1% solution at 0.5 ml/Kg/hr over the first hour and then if no untoward reaction is noted in the patient, gradually the rate of administration can be increased to 4 ml/Kg/hr until the total dose of 150 mg is given.

It should be understood that the examples and embodiments described herein are for illustrative purposes only and that various modifications or changes in light thereof will be suggested to persons skilled in the art and are to be included within the spirit and purview of this application and the scope of the appended claims.

References

Akashi, K., K. Nagasawa, T. Mayimi et al. (1990) "Successful treatment of refractory systemic lupus erythematosus with intravenous immuno-globulins" *J. Rheumatology* 17:375–379.

Blalock, J. E. (1990) "Complementarity of peptides specified by "sense" and "anti-sense" strands of DNA. *Trends in Biotechnol* 8:140–144.

Diamond et al., U.S. Pat. No. 4,690,905, issued Sep. 1, 1987.

Bayer, E. A. and M. Wilchek (1980) "The use of avidin-biotin complex as a tool in molecular biology methods" *Biochem Anal.* 26:1–45.

Davidson, A., A. Manheimer-Lory, C. Aranow R. Peterson, N. Hannigan, B. Diamond (1990) "Molecular characterization of a somatically-mutated anti-DNA antibody bearing two systemic lupus erythematosus-related idiotypes" *J. Clin. Invest.* 85:1401–1409.

Devey, M. E., K. Bleasdale, S. Lee, S. Rath (1988) "Determination of the functional affinity of IgG1 and IgG4 antibodies to tetanus toxoid by isotype-specific solid-phase assays" *J. Immunol. Method* 106:119–125.

Ebling, F., B. H. Hahn (1980) "Restricted subpopulations of anti-DNA antibodies in kidney of mice with systemic lupus: comparison of antibodies in serum and renal eluates" *Arthritis Rheum.* 23:392–403.

Gallo, G. R., T. Caulin-Glaser, M. E. Lamm (1981) "Charge of circulating immune complexes as a factor in glomerular basement membrane localization" *J. Clin. Invest.* 67:1305–1313.

Gauthier, V. J., M. Mannik, G. E. Striker (1982), "Effect of cationized antibodies in preformed immune complexes on deposition and persistence in renal glomeruli" *J. Exp. Med.* 156:766–777.

Goldblatt, D., L., vanEtten, F. J. van Milligen, R. C. Aalberse, M. W. Turner (1993) "The role of pH in modified ELISA procedures used for the estimation of functional antibody affinity" *J. Immunol. Methods* 166:281–285.

Jordan, S. C. (1989) "Intravenous gamma globulin therapy in systemic lupus erythematosus and immune complex disease" *Clin. Immunol. Immunopathol.* 53:S164–169.

Maier, C. C., H. N. B Moseley, S. R. Zhou, J. N. Whitaker, J. E. Blalock (1994) "Identification of interactive determinants on idiotypic-anti-idiotypic antibodies through comparison of their hydropathic profiles. Complementary peptides: application in immunology and as antibody mimetics" *ImmunoMethods* 5:107–113.

Mouthon, L., S. V. Kaveri, S. H. Spalter, S. Lacroix-Desmazes, C. Lefranc, R. Desai, M. D. Kazatchkine (1996) "Mechanisms of action of intravenous immune globulin in immune-mediated diseases" *Clin. Exp. Immunol.* 104: (suppl. 1)3–9.

Shoenfeld, Y., H. A. Teplizk, S. Mendlovic, M. Blank, E. Mozes, D. Isenberg (1989) "Short analytical review: the role of the human anti-DNA idiotype 16/6 in autoimmunity" *Clin Immunol Immunopathol* 51:313–325.

Silvestris, F., A. D. Bankhurst, R. P. Searles, R. C. Williams, Jr. (1984) "Studies of anti-F(ab')$_2$ antibodies and possible immunologic control mechanisms in systemic lupus" *Arthritis Rheum* 27:1387–1396.

Silvestris, F., P. Cafforio, F. Dammacco (1994) "Pathogenic anti-DNA idiotype-reactive IgG in intravenous immunoglobulin preparations" *Clin. Exp. Immunol.* 97:10–25.

Williams, Jr., R. C., C. C. Malone, G. R. Huffinan, F. Silvestris, B. P. Croker, E. Ayoub, S. Massengill (1995a) "Active SLE is associated with depletion of the natural generic anti-Id (anti-F(ab')$_2$) system" *J. Rheumatol.* 22:1075–1088.

Williams, Jr., R. C., C. C. Malone, F. Silvestris (1995b) "CDR molecular localization of possible anti-idiotypic anti-DNA antibodies in normal subjects, SLE patients and SLE first-degree relatives" *J. Lab and Clin Med.* 126:44–56.

Williams, Jr., R. C., A. D. Schnber, C. C. Malone, F. Silvestris, N. Hannigan, Klein-Gitelman, M. Namyst, R. A. Kyle (1994). "Expression of F4, 8.12, 3I and 16/6 anti-DNA idiotype-related antigens on cationic human IgG myeloma proteins." *Clinical Immunolog & Immunopathol.* 73:215–223.

Williams, Jr., R. C., C. C. Malone, K. Cimbalnik, F. Silvestris, K. H. Roux, L. Strelets (1995c) "Human IgG anti-F(ab')$_2$ antibody cross reacts with DNA and other nuclear antigens" *Arthnis Rheum* 38:730, S275.

I claim:

1. A human antibody composition, wherein said antibody composition comprises substantially purified and concentrated anti-idiotypic antibodies, or antigen binding fragments thereof, wherein said composition immunoreacts with idiotypes F4, 3I, 8.12 and 16/6 anti-DNA antibody determinants and which can bind to and inhibit self-reactive pathogenic autoantibodies.

2. The antibody composition, according to claim 1, wherein said anti-idiotypic antibodies arc immunoreactive with idiotypic determinants present or antibodies associated with systemic lupus erythematosus.

* * * * *

UNITED STATES PATENT AND TRADEMARK OFFICE
CERTIFICATE OF CORRECTION

PATENT NO. : 6,231,856 B1  
DATED : June 15, 2001  
INVENTOR(S) : Williams

Page 1 of 1

It is certified that error appears in the above-identified patent and that said Letters Patent is hereby corrected as shown below:

The above-captioned patent incorrectly includes this following paragraph regarding the National Institute of Health in the second paragraph of column one:

> "This invention was made with government support under National Institutes of Health grant number AR 1382-42A1. The government has certain rights in the invention."

The entire second paragraph in column one of the specification should be removed.

Signed and Sealed this

Eighth Day of January, 2002

*Attest:*

JAMES E. ROGAN  
*Attesting Officer*  *Director of the United States Patent and Trademark Office*